(12) United States Patent
Flatau (10) Patent No.: US 10,076,446 B2
(45) Date of Patent: Sep. 18, 2018

(54) NONINVASIVE SYSTEM AND METHOD FOR MITIGATING SLEEP-POSITION RELATED EYE LOADS

(75) Inventor: Alison Flatau, Potomac, MD (US)

(73) Assignee: Alison B. Flatau, Potomac, MD (US)

( * ) Notice: Subject to any disclaimer, the term of this patent is extended or adjusted under 35 U.S.C. 154(b) by 1055 days.

(21) Appl. No.: 14/349,954

(22) PCT Filed: Oct. 3, 2011

(86) PCT No.: PCT/US2011/054595
§ 371 (c)(1),
(2), (4) Date: Aug. 11, 2014

(87) PCT Pub. No.: WO2013/052031
PCT Pub. Date: Apr. 11, 2013

(65) Prior Publication Data
US 2015/0020814 A1    Jan. 22, 2015

(51) Int. Cl.
*A61F 9/04* (2006.01)
*A47G 9/10* (2006.01)

(52) U.S. Cl.
CPC ............... *A61F 9/04* (2013.01); *A47G 9/109* (2013.01); *A47G 9/1054* (2013.01); *A47G 9/10* (2013.01)

(58) Field of Classification Search
CPC ........ A47G 9/1054; A47G 9/109; A47G 9/10; A61F 9/04
USPC ........................................... 2/15; 5/636, 638
See application file for complete search history.

(56) References Cited

U.S. PATENT DOCUMENTS

| | | | | |
|---|---|---|---|---|
| 3,671,976 A | * | 6/1972 | Johnson | B63C 11/12 2/430 |
| 3,829,917 A | * | 8/1974 | De Laittre | A47G 9/109 5/636 |
| 4,349,925 A | * | 9/1982 | Macomber | A47G 9/10 5/491 |
| 4,788,728 A | * | 12/1988 | Lake | A47G 9/10 5/490 |
| 4,908,893 A | * | 3/1990 | Smit | A47G 9/10 5/636 |
| 5,018,231 A | * | 5/1991 | Wang | A47G 9/10 5/636 |
| 5,243,711 A | * | 9/1993 | Graham | A45D 44/12 2/430 |
| 5,245,709 A | * | 9/1993 | Shipcott | A61F 9/026 2/425 |
| 5,528,784 A | * | 6/1996 | Painter | A47G 9/10 5/636 |

(Continued)

FOREIGN PATENT DOCUMENTS

JP        3092724 U    3/2003

*Primary Examiner* — Khoa Huynh
*Assistant Examiner* — Jocelyn Bravo (57) ABSTRACT

When sleeping or resting in non-supine positions, reaction forces are distributed over areas of the face and head in contact with a surface, such as a mattress or arm, following a load path through at least one eye. Aspects of the disclosed system and method provide rigid to semi-rigid load bearing facial support configured to absorb and or distribute the reaction force exerted by a surface during non-supine rest or sleep to areas of padding best suited to absorb and or distribute said force such that the load path bypasses the eye, eye orbit, and or its surrounding anatomy to prevent or mitigate deformation, stress, strain, and or damage to the eye.

1 Claim, 6 Drawing Sheets

(56) References Cited

U.S. PATENT DOCUMENTS

| | | | | |
|---|---|---|---|---|
| 6,155,261 A | * | 12/2000 | Day | A61F 9/04 128/846 |
| 6,481,845 B1 | * | 11/2002 | Gazzara | A61F 9/026 2/436 |
| 6,530,659 B1 | * | 3/2003 | Marcum | A61F 9/02 351/156 |
| 6,574,809 B1 | * | 6/2003 | Rathbun | A47G 9/109 5/636 |
| 6,622,325 B1 | * | 9/2003 | Garza | A47G 9/10 5/636 |
| 6,842,924 B1 | * | 1/2005 | Walters | A47C 20/026 5/636 |
| 7,748,387 B1 | | 7/2010 | Vu et al. | |
| 8,572,780 B1 | * | 11/2013 | Watters | A47G 9/1054 5/490 |
| 2003/0188385 A1 | * | 10/2003 | Rathbun | A47G 9/109 5/636 |
| 2006/0143766 A1 | | 7/2006 | Ramsey | |
| 2009/0139031 A1 | * | 6/2009 | Davis | A47G 9/10 5/639 |
| 2013/0086749 A1 | * | 4/2013 | Crompton | A47G 9/1054 5/638 |
| 2013/0098364 A1 | * | 4/2013 | Davis | A47G 9/1081 128/206.21 |

\* cited by examiner

NONINVASIVE SYSTEM AND METHOD FOR MITIGATING SLEEP-POSITION RELATED EYE LOADS

FIELD OF INVENTION

Embodiments disclosed herein are directed to a system and method for mitigating or preventing deformation, stress, strain, and or damage to the eye, specifically during non-supine sleep or rest by providing a load path which bypasses the eye, eye orbit, including its surrounding anatomy to absorb and or distribute normal forces exerted on the face by a surface.

BACKGROUND OF INVENTION

When sleeping or resting in non-supine positions, normal forces are distributed over areas of the face and head in contact with a surface, such as a mattress or arm. For many non-supine positions this path is through at least one eye. The resulting load may cause deformation, stress, strain, and or damage to the eye, eye orbit, and or its surrounding anatomy. Yet another problematic effect of a load path passing through the eye area is shifting in the position of prescription orthokeratology (ortho-k) lenses prescribed for reshaping the cornea. That is, when forces are distributed over areas of the face and head in contact with a surface, with the load path through at least one eye, the force causes deformation of the eye and displacement or shifting of the lens. Such lens shift can negatively impact the effectiveness of corneal correction and often results in prolonged blurring of vision. This problem may be magnified when the lenses are worn throughout the night.

Ortho-k lens wearers who encounter shifting of lens position receive the challenging and impractical guidance of restricting sleep to supine (or avoid sleeping in non-supine) positions—e.g., lying on the back or having the face upward. A fundamental problem with guidance to avoid sleeping in non-supine positions is that many people are non-supine or side sleepers and will not be comfortable or be able to sleep in only a supine position. Moreover, merely shielding, covering, or surrounding the eye area with protection, without load-bearing structure that provides an alternative path bypassing the eye and surrounding soft tissues, will not adequately disperse loads introduced by sleeping or resting in non-supine positions. Thus, improper or superficial protections may not be able to prevent deformation, stress, strain, and or damage to the eye. Additionally, deformation, stress, and strain to the eye and surrounding tissue may inhibit the eye's ability to regulate intraocular pressure by contributing to sustained elevation of episcleral venous pressure, orbital venous pressure, trabecular meshwork outflow resistance, and or choroidal expansion. Impairment of the eye's ability to self-regulate intraocular pressure would in turn exacerbate symptoms of glaucoma, other eye diseases, or eye damage.

Pressure within the eye, or intraocular pressure (IOP), arises from a balance of the inflow of aqueous humor from ciliary secretion processes and outflow of aqueous humor through tissues such as the trabecular meshwork, as well as the magnitude of episcleral venous pressure. These three are balanced to provide sufficient pressure within the eye (typically IOPs of 10-21 mm Hg above atmospheric pressure) so that the eye globe remains inflated. This balance has been quantitatively defined by Goldman in the 1950's as: $IOP=F/C+EVP$, where F is aqueous humor inflow, C is the outflow facility, EVP is episcleral venous pressure and IOP is the intraocular pressure. Elevation of episcleral venous pressure when in a horizontal position has been associated with an increase in nighttime intraocular pressure. Additional increases in episcleral venous pressure and or a decrease in aqueous outflow associated with loads on the eye, eye orbit, and surrounding anatomy due to sleep position would contribute to an additional increase in the intraocular pressure. An increase in orbital venous pressure due to sleep position induced loads could also contribute to an increase in outflow resistance and disrupt the intraocular pressure self-regulation process needed for return of intraocular pressure back to normal healthy levels. Expansion of the choroid circumference or thickness due to sleep position related deformation, stress or strain of the eye could also contribute to an increase in outflow resistance and further disrupt the ability of the eye to self-regulate intraocular pressure and an elevation in intraocular pressure. In summary, there are a variety of mechanisms whereby loads on the eye could produce an increase episcleral venous pressure and or a decrease aqueous outflow and a disruption of the ability to self-regulate IOP, causing IOP to increase.

A well-established method for lowering IOP levels utilizes the Honan Intraocular Pressure Reducer, a pre-surgical device which compresses the eye and is used specifically to lower IOP and thereby reduce the risk of explosive vitreous loss upon incision. The Honan Intraocular Pressure Reducer works by applying a compressive pressure of between 20 and 30 mm Hg to the eye. This external pressure causes an increase in the rate of fluidic outflow through the trabecular meshwork relative to the rate of fluid inflow, without affecting the episcleral venous pressure and thereby lowering the internal eye pressure, i.e. lowering IOP. See Peter J. McDonnell, *The Honan Intraocular Pressure Reducer*, 103 Archives of Opthalmology 422, 422-425 (1985); James El Morgan et al., *Intraocular Pressure After Peribulbar Anaesthesia: Is the Honan Balloon Necessary?*, 79 British Journal of Opthalmology 46, 46-49 (1995).

There is a distinction between the direct application of pressure to the eye produced by this common pre-surgical practice, which applies pressure directly to the eye and eyelid, and the deformation, stress and strain of the eye, eye orbit, and its surrounding anatomy introduced by the loads on the eye associated with side- and face-down sleep positions. Sleep-position related forces can raise episcleral and orbital venous pressure, increasing trabecular meshwork outflow resistance along with choroidal expansion, all of which may contribute to sustained IOP elevation due to impairment of the ability of the eye to self-regulate back to normal healthy levels. Such sustained IOP increase, over and above the known increase in IOP associated with being in a horizontal position, could contribute to serious eye damage including but not limited to glaucomatous eye damage and deformation.

Normal IOP levels are in the range of 10-21 mm Hg. Normal IOP levels vary somewhat according to the time of day, usually being higher in the morning than later in the day. IOP levels of at least ~10 mm Hg are needed for the eye globe to retain its shape. Tonometry is used to measure IOP indirectly from observation of cornea surface deflections in response to a known force. Currently, IOP cannot be measured while a person is sleeping, although sensors that can be used for this are under development—e.g., Sensimed's Triggerfish® sensors. Factors generally considered and or known to be correlated with the manifestation of glaucoma include low blood pressure, high blood pressure, thin corneal walls, and low blood supply to the optic nerve as well as a number of other physiological considerations and bio-chemical considerations. Generally, the first course of treatment for glaucoma patients includes eye drops to lower IOP to normal levels—e.g., prostaglandins in conjunction with beta blockers.

Glaucoma is an eye disorder where the optic nerve suffers damage and retinal ganglion cells die. Glaucoma permanently impacts vision, progressing to blindness if left untreated and is one of the leading causes of blindness worldwide. The cause of glaucoma is not known. Optic nerve damage due to glaucoma is often associated with an increase in intraocular pressure (IOP) to pressures above 21 mm Hg. However, some glaucoma patients with optic nerve damage do not exhibit elevated IOP levels. This type of glaucoma is sometimes called normal-tension or low-tension glaucoma. Several recent studies suggest IOP-related stress, strain, strain rates etc. of optic nerve head tissues contribute to glaucomatous cell damage. See Claude F. Burgoyne et al., *The Optic nerve head as a Biomechanical Structure: A New Paradigm for Understanding the Role of IOP-Related Stress and Strain in the Pathophysiology of Glaucomatous Optic nerve Head Damage*, 24 Progress in Retinal and eye Research 39, 39-73 (2005); Ian A. Sigal et al., *Predicted Extension, Compression and Shearing of Optic Nerve Head Tissues*, 85 Experimental Eye Research 313, 31-322 (2007); Ian A. Sigal et al., *Biomechanics of the Optic Nerve Head*, 88 Experimental Eye Research 799, 799-807(2009); Michael D. Roberts et al., *Correlation between Local Stress and Strain and Lamina Cribosa Connective Tissue Volume Fraction in Normal Monkey Eyes*, 51 Investigative Ophthalmology & Visual Science 295, 295-307 (2010); Barry Quill et al., *The Effect of Graded Cyclic Stretching on Extracellular Matrix-Related Gene Expression Profiles in cultured Primary Human Lamina Cribrosa Cells*, 52 Investigative Ophthalmology & Visual Science 1908, 1908-15 (2011); Richard E. Norman et al., *Finite Element Modeling of the Human Sclera: Influence on Optic Nerve Head Biomechanics and Connections with Glaucoma*, 93 Experimental Eye Research 4, 4-12 (2011).

Non-degenerative and degenerative eye damage may be reflected by load bearing pressure on the eye(s). For example, a person lying on a traditional mattress experiences pressures on the eye due to the weight of the head being uniformly distributed over the side of the face in contact with the mattress. The weight of the head is supported by the portion of the face resting on the mattress, and this portion of the face bears the resulting reaction force. The reaction force on the face is equal but in opposite direction to the weight of the head as: N=mg, where m is the mass of the head, and g is the gravitational constant, ~9.81 Newtons/kg. The reaction force N in this example represents the force applied by the mattress against the head that prevents it from sinking through the surface. In many non-supine positions, the area of the face that rests on a surface includes at least one eye. Transmission of this force N or load through the eye area results in forces on tissues.

To illustrate the forces acting on the eye in these common positions, the following values for weight and surface area are employed. These values are approximations utilized to establish a force balance model of pressure exerted on the eye and actual values may vary from individual to individual. Assuming that the approximate average value for a human head weight is 10.0 pounds (lbs), it is estimated that the surface area in contact with a surface while resting or sleeping on the side will be rectangular in shape with dimensions of roughly 6.5 inches by 8.0 inches, with a surface area of 52.00 square inches. In this scenario, the weight of the head resting on the side of the face produces an average pressure (force per area) over the surface of the side of the face of 10 pounds per 52 square inches. This is equivalent to an average pressure of ~0.19 pounds per square inch (psi) or ~9.9 mm Hg. Newton's third law states that for every force there is a reaction force, equal in magnitude and acting in the opposite direction. This law is applied to estimate the increase in intraocular pressure due to the weight of the head pressing the eye against a surface during sleep. The human eye as a sphere with an approximate radius of 0.47 inch (12.0 mm) and thus a surface area of 2.8 $in^2$. Assuming that when sleeping or resting approximately one third of the surface area of the eye is in contact with a surface that is exposed to a pressure of 0.19 psi, the pressure acts on the eye over a surface area of 0.93 $in^2$, producing forces of 0.18 lb dispersed over the 2.8 $in^2$ of the eye surface area. It is estimated, for purpose of this example, that this would cause an increase in intraocular of 0.065 psi or 3.3 mm Hg for the non-supine, side sleep or rest scenario. Given that the Honan pressure reducer is operated so as to apply a pressure of 20-30 mm Hg to the eye for periods of 5-30 minutes without causing damage to the eye, this 3 mmHg increment in IOP produced by the a pressure of ~10 mm Hg from the weight of the head should be readily accommodated by a self-regulatory increase in aqueous outflow.

Various devices, goggles, eye-glasses and protective eye-gear are known in the art. For example, U.S. Pat. No. 6,155,261 to Day discloses a device that purports to assist with relieving elevation of IOP during sleep. U.S. Pat. No. 5,213,241 to Dewar et al. discloses a device that is used to protect the eye during physical activity. Sleep masks such as U.S. Pat. No. 5,343,561 to Adamo and other eye shield devices such as U.S. Pat. No. 5,183,059 to Leonardi appear to position a covering across the bony orbital rim of the wearer's eye but do not appear to absorb and or distribute normal forces exerted by a surface through a load path which bypasses the eye and surrounding tissue. However, none of these provide the necessary force distribution, force alleviation, and deformation avoidance attributes required to mitigate or prevent deformation, stress, strain, and or damage.

SUMMARY OF THE INVENTION

The embodiments disclosed herein overcomes both physiological and mechanical problems associated with forces following a load path through at least one eye during sleep or rest in non-supine positions by providing an alternative load path bypassing the eye, eye orbit, and or its surrounding anatomy to mitigate or prevent deformation, stress, strain, and or damage.

It is an object herein to provide a non-invasive system and method that creates a load path which bypasses the eye to mitigate or prevent deformation, stress, strain, and damage to the eye, eye orbit, and or its surrounding anatomy during non-supine sleep or rest.

It is yet another object to provide a non-invasive device that includes a load transferring support structure that creates a load path which bypasses the eye, eye orbit, and its surrounding anatomy during sleep or rest in non-supine positions to prevent or mitigate deformation, stress, strain, and or damage to the eye.

It is yet another objective to provide a device that prevents shifting in the position of orthokerantology contact lenses worn during sleep or rest in non-supine positions by creating a load path bypassing the eye.

It is yet another objective to provide a system and method that may be utilized in the treatment and prevention of disruption to the self-regulation of intraocular pressure, glaucoma and other degenerative and non-degenerative eye diseases.

DETAILED DESCRIPTION OF THE EMBODIMENTS

The embodiments disclosed herein are directed to a non-invasive system and method for structural load-transfer that allows normal forces to bypass the eyes. The system includes a device that may be worn during sleep so that a load, such as the weight of the head, is transferred though a load path that bypasses eye. Thus, the present system prevents loads that arise when sleeping from causing deformation of the eye and/or damage to the eye due to deformation, stress, strain and/or degradation of the eye(s)' ability to regulate intraocular pressure (IOP) such as would result from elevation of the trabecular meshwork outflow resistance, elevation of episcleral venous pressure, elevation of orbital venous pressure and/or enlargement of the choroid. The embodiments may be utilized for long-term use, such as during sleep for durations of 8 hours or more.

The embodiments disclosed herein are also directed to a non-invasive system and method for mitigating deformation and eye damage, having particular utility for those who experience position shifting of prescription orthokeratology (ortho-K) contact lenses due to deformation of the eye while sleeping.

The embodiments disclosed herein also provides a non-invasive system and method for assisting those diagnosed with glaucoma and/or degenerative eye diseases marked by conditions that result in permanent optic nerve damage, those which family histories of glaucoma who display evidence of contributory conditions such as thin retinal walls, optic nerve cupping, etc. By preventing external forces from deforming the eye during sleep, load transfer paths mitigate load-induced deformation of the eye, which in-turn mitigates stress and strain of cells that form the load-bearing portions of the eye walls, as well as the potential for increased outflow resistance of the trabecular meshwork.

As will be understood by one of ordinary skill, the present system and method may be utilized with traditional therapies for treating a variety of degenerative and non-degenerative eye ailments.

Figure 1:
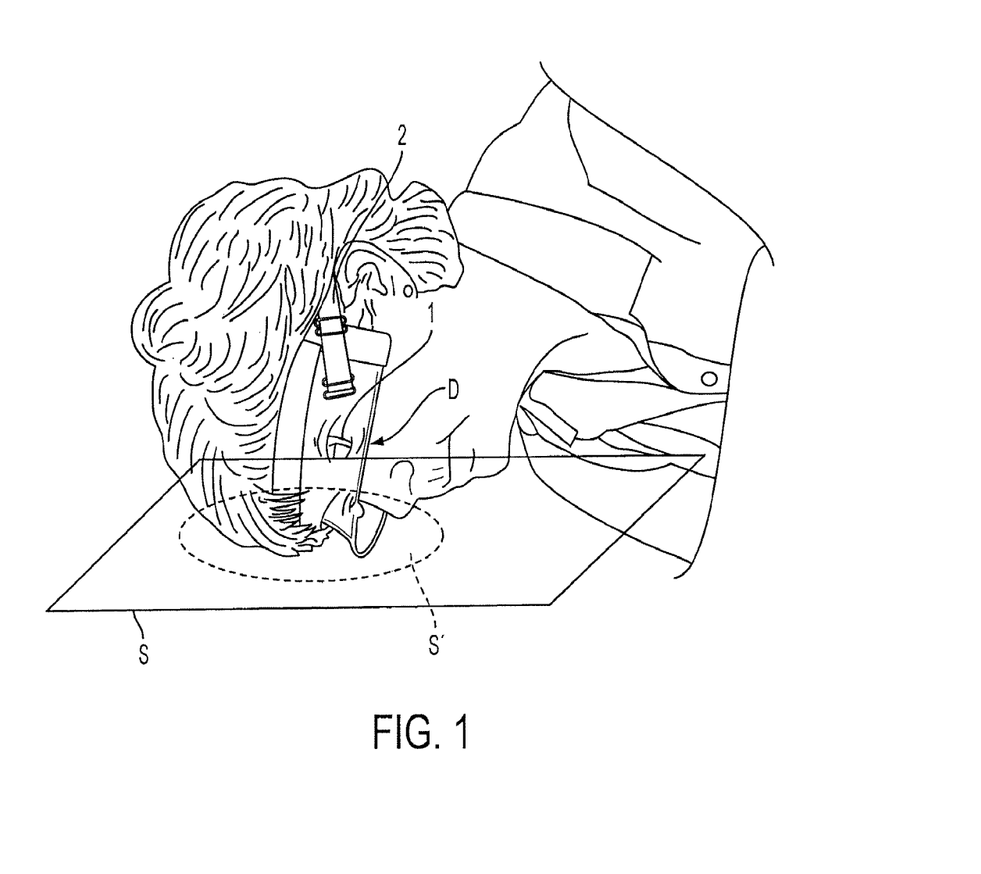
FIG. 1 shows the support-to-surface interface with respect to the surface plane when the wearer is sleeping or resting.

FIG. 1 shows a wearer of the system disclosed herein. The illustrated system includes a device D having a front portion 1 and a back stabilizing portion 2. The support-to-surface interface S' with respect to the surface plane S, as shown in FIG. 1, is the surface against which the wearer of device D is sleeping or resting. The surface S' may refer to any resting or sleeping surface such as a mattress or pillow. The weight of the head is supported by the portion of the face resting on the mattress, and this portion of the face bears the resulting reaction force N. For the purposes of this disclosure, the reaction force N on the face is equal but in opposite direction to the weight of the head. The surface S' exerts a force equal and opposite in direction against the wearer's face proportional to the force of the wearer against the surface. Device D provides an alternative load path to absorb and or distribute such reaction forces N that would otherwise be exerted against the wearer's face by way of a path including the wearer's eye during sleep or rest. In use, device D of the system ensures adequate ventilation to the cornea and mitigates or prevents stress, strain, and or deformation of the eye.

Figure 2:
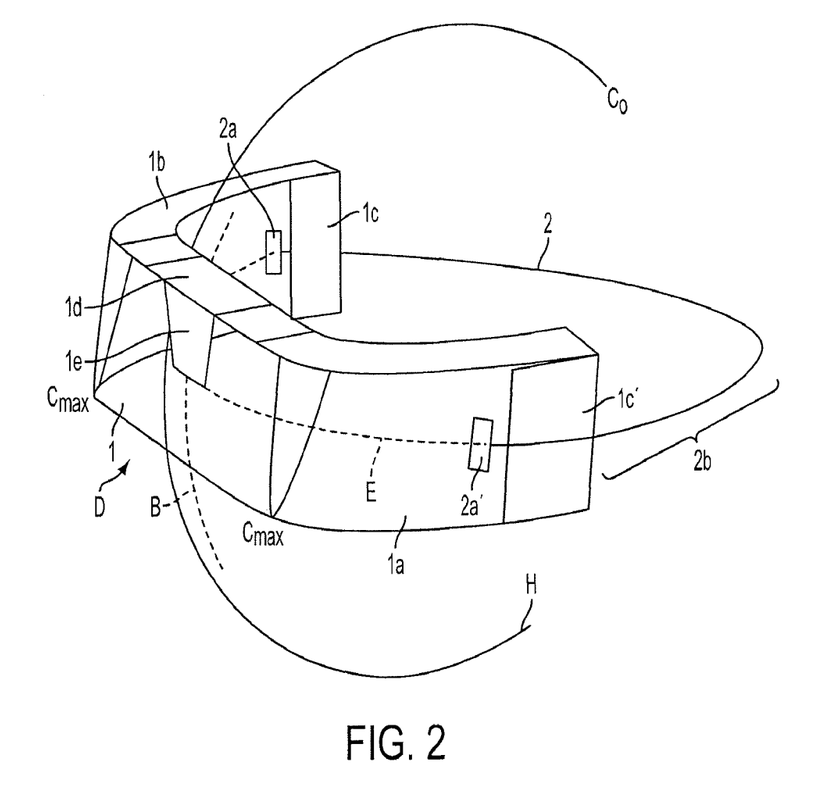
FIG. 2 shows a partially rotated view of the system illustrating the load transferring support structure.

As shown in FIG. 2, the front portion 1 of device D includes a load transferring support structure 1a configured to fit snugly around the front of the wearer's face as provided by padding 1b, side padding 1c and 1c', forehead padding 1d, and nose bridge padding 1e. The load transferring support structure 1a (also referred to herein as "support structure 1a") may be constructed as a contoured, translucent barrier made of e.g., plastic, acrylic, metals, composite, as selected to support the maximum loads likely to be encountered during sleep or rest without deforming. Load transferring support structure 1a may also be a contoured, translucent barrier that provides continuous coverage from the longitude of the nasal spine to the forehead boss or frontal bone. Alternatively, support structure 1a may be a contoured, translucent barrier that provides partial coverage of the wearer's anatomical features. By serving as load-bearing structure, support structure 1a allows for external loads to bypass the eye by distributing reaction forces N and loads to padded areas 1b through 1e corresponding to bony facial structure such as the nasal bone, zygomatic bone, and forehead, while allowing ventilation of the eye area and preventing contact between the eye and the surface. Support structure 1a provides sufficient outward projection to accommodate the nasal bone and structure of the nose, to which additional padding may be applied to avoid pressure points.

Support structure 1a may also be configured of a meshwork structure made from wire, plastic, a fiber matrix or the like such that the structure is sufficiently rigid to bear loads described previously. The support structure 1a may be configured to provide continuous coverage from the longitude of the nasal spine to the forehead boss or frontal bone. Alternatively, support structure 1a may also be configured to provide partial coverage of anatomical features and serve as a load-bearing structure thereby enabling external loads to bypass the eye and be distributed over the nasal bone, zygomatic bone, forehead, while also allowing optimal ventilation of the eye area. Additionally, load transferring support structure 1a may include a translucent portion for visibility. The translucent portion of support structure 1a may be tinted and or may have a prescription applied in the manner of a conventional eye glass lens. The device D is intended to be worn for long periods of time, typically 8 hours or more and when muscles are relaxed. It is under these circumstances when maximum force loads are likely to be encountered.

Figure 3:
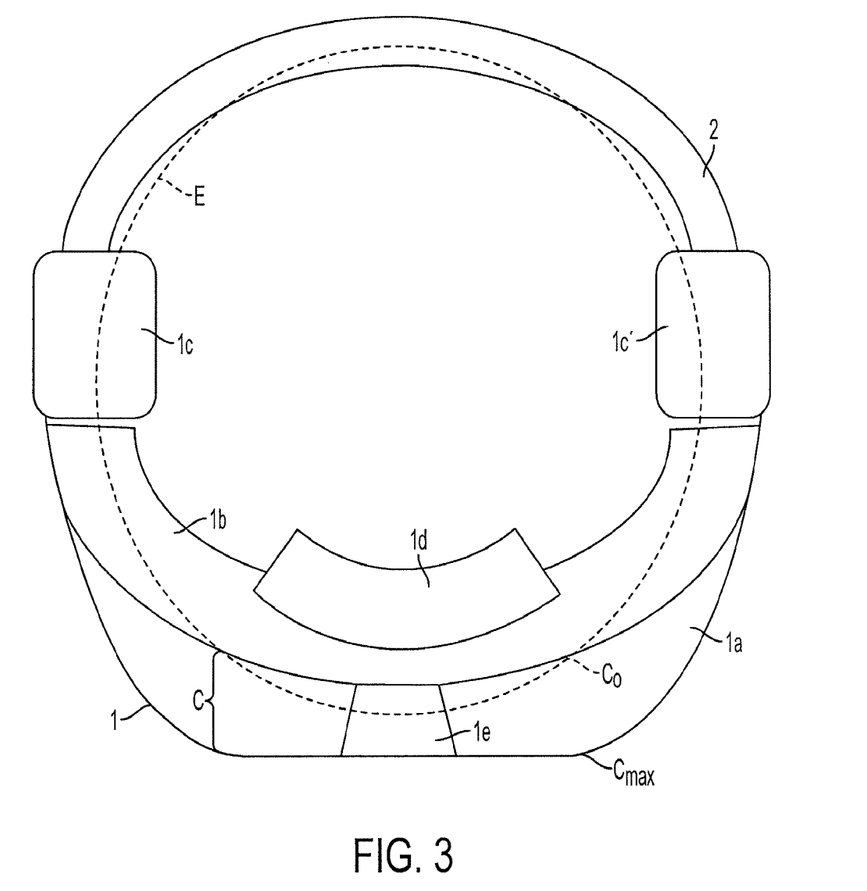
FIG. 3 shows an overview of the system illustrating the load transferring support structure.

The device D includes a back stabilizing component portion 2, as shown in FIG. 2 and FIG. 3. Stabilizing component 2 is utilized for securing the front portion 1 such that the wearer may securely retain the device D on their face. Support structure 1a may include one or more apertures, such as apertures 2a and 2a', through which one or more stabilizing components 2 may be secured. Component 2 may be constructed so as to be adjusted 2b for individual comfort. The component 2 may be constructed of e.g., elastic fabric, rayon, nylon, rubber or other tightening or adjustable material. In another embodiment, the stabilizing component of 2 may include a helmet or cap attached to support structure 1a. The ability to properly fit the device D on the wearer's face as secured by stabilizing component 2 in addition to padding 1b through 1e is a feature of the disclosed embodiments since the wearer may roll, toss or turn, or else be positioned on their side, face down, or with an object e.g., an arm or pillow resting on or against the support-to-surface interface plane S'.

Front portion 1 includes an upper padded portion 1b that conforms to the upper surface of front portion 1 and the wearer's face. Front portion 1 also includes side padded portions 1c and 1c' configured to be positioned on each side of the wearer's face. Front portion 1 also includes an interior position having a padded portion 1d as shown in FIG. 2 to absorb loads channeled to the system's center and approximately corresponding to the rigid underlying anatomical structure of the glabellar region of frontal bone. Front portion 1 also includes a medially padded portion 1e that is configured to fit the wearer's face snugly in the area of the nose bridge. In use, the device D is placed on the wearer's face thereby providing a load path which bypasses the eye, eye orbit, and its surrounding anatomy during sleep or rest in non-supine positions. Front portion 1 is constructed of material sufficiently rigid to bear loads, such as the weight of the head by providing a complete or partial load transferring support structure 1a to the surface S' interposed with padding 1b through 1e configured to fit snugly on the wearer and absorb and distribute loads exerted by the support-to-surface interface S'. The surface S' may include but is not limited to a mattress surface, a pillow or the like. The device D absorbs and distributes the reaction force exerted by surface S' such that of those loads bypasses the eye. The front portion 1 may distribute such loads across e.g., the forehead, cheekbones, temples, nasal bridge.

Additionally, the front portion 1 may distribute the load over load-bearing structures 1a and the padding portions 1b through 1e. Padding portions 1b through 1e are constructed to be interposed between support structure 1a and the wearer and made of deformable or semi-deformable material including but not limited to low to high density foam, semi-solids, fabric, synthetic fiber, gel and rubber. Padding portions 1b through 1e are configured to absorb and distribute forces across the surface area of the support 1 such that the load path bypasses the eye. Additionally, padding portions 1b through 1e are interposed between the support 1a and the wearer's facial structure, e.g., across the forehead and or spanning the nasal bridge and cheek bones, in order to distribute and absorb loads such that they bypass the eye area and are channeled to anatomical features better suited to bear loads, e.g., with bony structure, than soft-tissues and facial muscle, which may otherwise lead to deformation of the eye and or degradation of the eye(s)' ability to regulate IOP. Impairment of the eye(s)' ability to regulate IOP may result from independent or combined trabecular meshwork outflow resistance increase, episcleral venous pressure increase, orbital venous pressure increase and choroidal expansion.

Applying padding such as padding 1d corresponding in position to the forehead boss or glabella regions projects the support-to-surface interface plane S' towards the surface plane S, and directs external forces to anatomical structure particularly suitable to bear loads without creating uncomfortable pressure points. These anatomical structures include but are not limited to the forehead, temples, cheekbones, and chin. In a preferred embodiment, padding 1c is interposed between support structure 1a and the wearer's head e.g., at the parietal and temporal bones, extending downwards towards the wearer's jaw e.g., zygomatic bone, to distribute and absorb direct or indirect loads such that they bypass the eye and provide optimal stability during movement or rotation by providing a snug fit to the wearer's face.

As further shown in FIG. 2 through FIG. 5, front portion 1 creates clearance C between the eye(s) and the surface S'. In FIG. 2, H is the anterior plane of the head including the face and vertical plane of the nose bridge B. E is the axial eye plane running from ear to ear horizontally through the eye area as shown in relation on the system to illustrate the amount of clearance C between the eye and surface S' created by wearing the system. At the intersection of the head H and eye E planes the clearance is zero ($C_0$) because this represents the surface of the eye. Front portion 1 includes a load transferring support structure 1a serving as a barrier to the surface S' yielding clearance C between the eye and the support-to-surface interface of S' as large as $C_{max}$ (i.e., the maximum clearance). Clearance C may vary depending on position, degree of force, rotation, depression of padding, and other factors.

Figure 4:
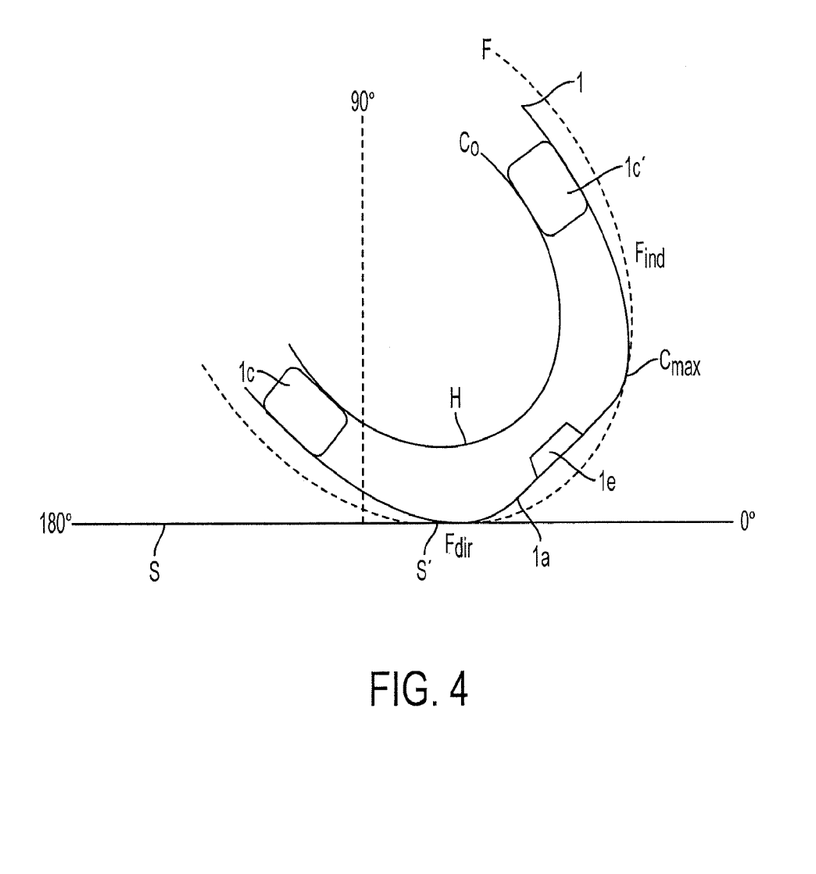
FIG. 4 shows a cross-section of the system at the eye plane when resting on a surface.
Figure 5:
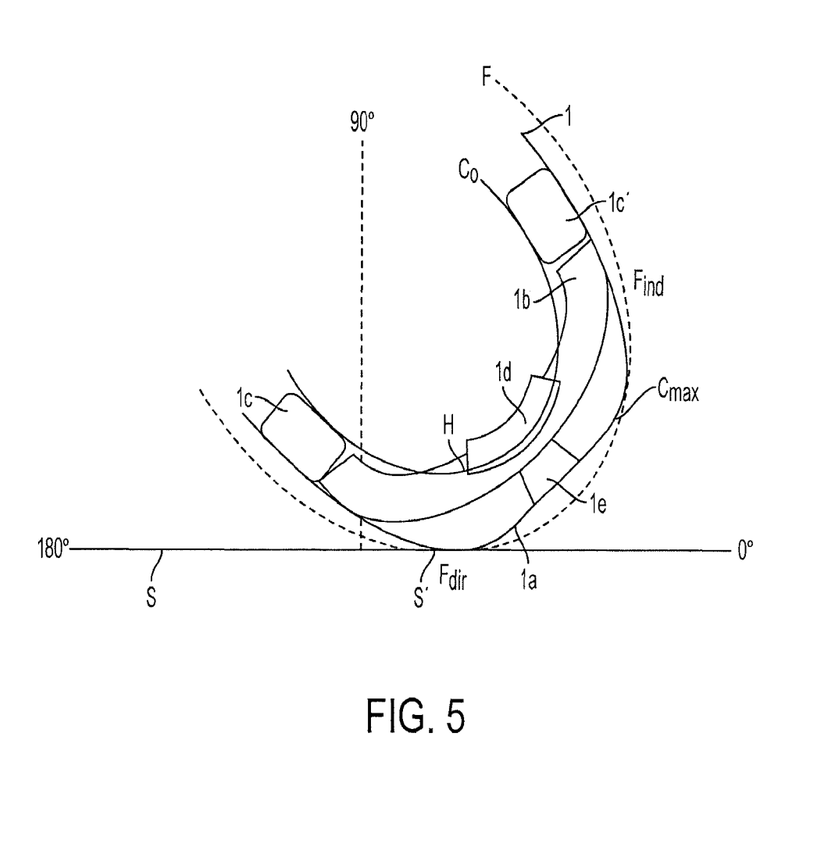
FIG. 5 shows an overview of the system when resting on a surface.

As shown in FIG. 4 and FIG. 5, force distribution F across the device D follows a load path along the front portion 1 by providing a load transferring support structure 1a to absorb forces directly and indirectly with padding 1b through 1e interposed between support structure 1a and the wearer. Forces are thus directed to structure particularly suitable to bear loads e.g., forehead by padding portions 1b and 1d, nasal bridge by padding 1e, and jaw or zygomatic bone by padding portions 1c and 1c'. Reaction forces N exerted by the surface S' bypass the eye area by clearance C. The force distribution F across the device D is further characterized by direct forces $F_{dir}$ including vertical forces exerted against the front portion 1 by the surface S' in addition to indirect forces $F_{ind}$ due to moment(s) introduced by the angle of rotation along the surface plane S. Forces are balanced according to the scheme of support structure 1a interposed with padding 1b through 1e to provide a load path which bypasses the eye by clearance C to avoid direct contact as well as create alternative force distribution along F to mitigate or prevent stress, strain, deformation, and pressure against soft tissue or facial muscle.

Additionally, support structure 1a and padding portions 1b through 1e may be customized or individualized by obtaining an impression of the wearer's face. Memory foam, rigidized foam castings, and the like may be utilized to provide the customization feature. As will be understood to one of ordinary skill the load transferring support structure 1a and the padding portions 1b through 1e are of a dimension and configuration so as to provide a balance between rigidity, flexibility, elasticity, softness, density, weight such that it provides the optimal load bearing structure commensurate with the scope and objectives of the disclosed embodiments.

Additionally, front portion 1, as shown in FIG. 2 through FIG. 5, is constructed so as to absorb and distribute loads associated with pressure on the eye. In one manner, front portion 1 covers the eye area by clearance C while padded sections 1b through 1e act to project load bearing anatomical structures particularly suited to bear loads so as to intercept reaction forces N such that they bypass the eye and are thus distributed or absorbed by the device D.

In another manner, front portion 1 is also configured to absorb and distribute both direct $F_{dir}$ and indirect $F_{ind}$ force vectors associated with sustained physiological deformation, stress and strain on the eye, eye orbit, and its surrounding anatomy that contribute to degenerative and non-degenerative eye disease such as glaucoma by distributing and absorbing reaction forces. N. These diseases include but are not limited to impairment of the eye's ability to regulate IOP as associated with sustained elevation of episcleral venous pressure, orbital venous pressure, trabecular meshwork outflow resistance, and choroidal expansion. In a preferred embodiment, device D is constructed so as to alleviate sustained physiological deformation, stress and strain on the eye by channeling forces to anatomical structures particularly suitable to bear loads by distributing direct forces $F_{dir}$ and indirect forces $F_{ind}$ along the support structure 1a to be absorbed by padding 1b through 1e in addition to creating clearance C to avoid direct contact. The clearance C margin and alternative load path with force distribution F ensure that stress is not exerted on soft tissue or anatomy surrounding the eye since forces are directed to anatomical structure particularly suitable to bear loads by way of padding e.g., forehead by padding portions 1b and 1d, nasal bridge by padding 1e, and jaw and zygomatic bone by padding portions 1c and 1c'.

Figure 6:
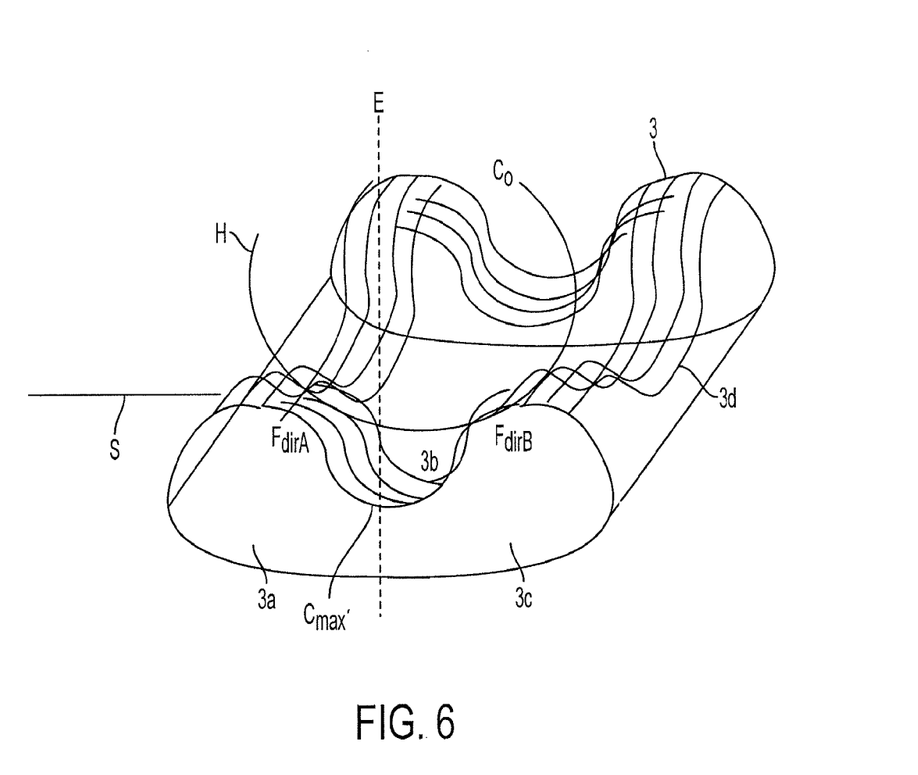
FIG. 6 shows the support system.

The system disclosed herein also provides for a force distribution support 3 as shown in FIG. 6. The force distribution support 3 may be utilized alone or in combination with device D to provide force distribution commensurate with the scope of the embodiments discussed above. As shown in FIG. 6, the upwards facing profile of distribution support 3 is contoured such that it provides a raised portion 3a to support the forehead, a concave portion 3b yielding a clearance C along the eye plane E, a second raised portion 3c to support the cheek and chin, and a second concave portion 3d to meet and support the neck. The downwards facing profile of support 3 is flat to rest squarely and securely on the surface plane S, yielding a support-to-surface interface S' area capable of further distributing and absorbing the reaction force N. Portions 3a through 3d may be contiguous and gradually sloping, thereby allowing the force distribution support 3 to provide a uniform load distribution over the selected regions of the face and neck of the wearer and away from the eye.

As shown in FIG. 6, force distribution support 3 supports the forehead, cheek, chin, and neck regions at 3a through 3d, respectively. The depression of 3b yields a clearance C between the eye and the support-to-surface interface of S' as large as $C_{max'}$ (i.e., the maximum clearance). Clearance C may vary depending on position, degree of force, rotation, depression of padding, and other factors. Concave portion 3b is further constructed such that the eyes of the wearer receive no contact in non-supine sleep or rest positions, such as in a slide-sleeping or face down position, by a maximum level of clearance $C_{max'}$. In this manner, force distribution support 3 may be used in conjunction with device D to provide optimal load bearing support bypassing the eyes, commensurate with the objectives described herein. As will be understood to one of ordinary skill, support 3 is constructed so as to provide a balance between rigidity, flexibility, elasticity, softness, density, weight such that it provides the optimal load dispersal and can be constructed of materials that provide a balance between cushioning and load distribution commensurate with the scope of the embodiments disclosed herein. Such materials may include but are not limited to foams, cotton, polyesters and hypoallergenic materials.

In a preferred embodiment, support 3 is constructed of a continuous hypo-allergenic foam pillow sufficiently rigid to comfortably support the forehead at 3a, cheek bone and chin at 3c, and neck at 3d while providing maximum clearance $C_{max'}$ along the eye plane E at 3b. Raised portions 3a and 3b are configured to protrude in correspondence with bony anatomical structure particularly suitable to bear loads, e.g., at the forehead boss and glabellar regions corresponding to 3a and at the zymoatic bone spanning portions of the cheek and chin corresponding to 3b.

Reaction force N exerted through the upwards facing profile of support 3 yields a unique force distribution profile selectively channeled through the raised portions of 3a and 3c and not through the eye plane E at the depression of 3b. As shown in FIG. 6, the force normal bypasses the eye plane E yielding a maximum clearance $C_{max'}$ where the eye, eye orbit, and surrounding anatomy would otherwise be in contact with the surface S'. Instead, forces are channeled to the raised portions 3a and 3c where the reaction force exerted by 3a against the user's forehead is $F_{dirA}$ and the reaction force exerted by 3c against the user's check and chin is $F_{dirB}$.

I claim:

1. A protective eye shield, designed solely to provide a load path that prevents external forces from deforming a wearer's eyes during sleep, comprising:
   a front portion and a back stabilizing portion;
   said front portion comprising:
      a load transferring support structure designed solely to support a load of the wearer's head and distribute both direct and indirect force vectors away from the wearer's eyes, eye orbits, and surrounding soft tissue when the wearer is in a non-supine sleep position;
      said load transferring support structure designed solely to prevent stress, strain or deformation of the wearer's eyes;
      said load transferring support structure constructed as a contoured barrier including one of plastic, acrylic, metal, or a composite;
      said load transferring support structure providing at least partial coverage of the wearer's face from the forehead to the nasal spine, without extending below the wearer's nasal spine;
      said load transferring support structure comprising an outward projection designed solely to create a clearance between the wearer's eyes and a sleeping surface to avoid direct contact of forces with the wearer's eyes, eye orbits, and surrounding soft tissues;
      said contoured barrier further comprising padding portions configured to conform to and contact the wearer's forehead boss, temporal regions, and nasal bone when the eye shield is worn in the non-supine sleep position; and
   said back stabilizing portion comprising a component designed solely to secure said front portion to the wearer's face, said securing component constructed of one of elastic fabric, rayon, nylon, or rubber;
   wherein when the eye shield is worn, external forces bypass the wearer's eye area due to said clearance between the wearer's eyes and the sleeping surface, and are redirected to the wearer's forehead boss, temporal regions, and nasal bone via said padding portions, wherein said padding portions are designed solely to absorb and distribute said forces.

* * * * *